US007360896B2

(12) United States Patent
Liang et al.

(10) Patent No.: US 7,360,896 B2
(45) Date of Patent: Apr. 22, 2008

(54) FUNDUS CAMERA FOR WIDE FIELD OF VIEW AND SMALL PUPIL

(75) Inventors: Rongguang Liang, Penfield, NY (US); Jeffery R. Hawver, Marion, NY (US)

(73) Assignee: Carestream Health, Inc., Rochester, NY (US)

( * ) Notice: Subject to any disclaimer, the term of this patent is extended or adjusted under 35 U.S.C. 154(b) by 149 days.

(21) Appl. No.: 11/247,100

(22) Filed: Oct. 11, 2005

(65) Prior Publication Data
US 2007/0081127 A1   Apr. 12, 2007

(51) Int. Cl.
A61B 3/14   (2006.01)
A61B 3/00   (2006.01)
(52) U.S. Cl. ........................... 351/206; 351/200
(58) Field of Classification Search ............... 351/206
See application file for complete search history.

(56) References Cited

U.S. PATENT DOCUMENTS

| 4,247,176 A |  | 1/1981 | Ito |
|---|---|---|---|
| 4,558,932 A | * | 12/1985 | Nunokawa ............... 351/206 |
| 4,838,680 A |  | 6/1989 | Nunokawa |
| 4,848,897 A | * | 7/1989 | Aizu et al. ............... 351/221 |
| 5,572,266 A |  | 11/1996 | Ohtsuka |
| 5,713,047 A |  | 1/1998 | Kohayakawa |
| 5,742,374 A |  | 4/1998 | Nanjo et al. |
| 5,943,116 A |  | 8/1999 | Zeimer |
| 6,296,358 B1 |  | 10/2001 | Cornsweet et al. |
| 6,546,198 B2 |  | 4/2003 | Ohtsuka |
| 6,636,696 B2 |  | 10/2003 | Saito |
| 2006/0077347 A1 | * | 4/2006 | Liang et al. ............... 351/221 |

* cited by examiner

Primary Examiner—Jordan M. Schwartz
Assistant Examiner—James C Jones (57) ABSTRACT

A fundus camera (10) obtains a retinal image using a light source (62), a ring aperture (58) conjugate to the cornea, and a first aperture (54) conjugate to the iris. An apertured mirror (52) redirects the ring illumination toward the eye. An objective lens (50) between the apertured mirror (52) and the eye has an entrance pupil between the iris and the cornea of the eye. The objective lens (50) directs the ring illumination into the pupil of the eye and directs a reflected image-bearing light from the retina through the apertured mirror (52). A second aperture (64), conjugate to a plane between the cornea and the iris of the eye, forms an aperture stop for the reflected image-bearing light. A third aperture (68) is conjugate to the cornea for blocking light reflected. A sensor (70) provides an image of the retina.

5 Claims, 15 Drawing Sheets

FUNDUS CAMERA FOR WIDE FIELD OF VIEW AND SMALL PUPIL

FIELD OF THE INVENTION

This invention generally relates to electronic imaging apparatus for fundus imaging and more particularly relates to an improved fundus imaging apparatus suitable for smaller pupil diameters.

BACKGROUND OF THE INVENTION

Fundus camera imaging is acknowledged to be an important diagnostic tool for detection of various conditions affecting the eye, including diabetic retinopathy and macular degeneration. Various embodiments of fundus imaging apparatus are disclosed, for example in U.S. Pat. No. 5,713,047 (Kohayakawa); U.S. Pat. No. 5,943,116 (Zeimer); U.S. Pat. No. 5,572,266 (Ohtsuka); U.S. Pat. No. 4,838,680 (Nunokawa); U.S. Pat. No. 6,546,198 (Ohtsuka); U.S. Pat. No. 6,636,696 (Saito); U.S. Pat. No. 4,247,176 (Ito); U.S. Pat. No. 5,742,374 (Nanjo et al.); and U.S. Pat. No. 6,296,358 (Comsweet et al.)

While these patents attest to continuous improvements in fundus camera design, there are still significant hurdles to obtaining good quality images from these devices. Fundus cameras must solve the fairly difficult problem of simultaneously illuminating the retina through the pupil and obtaining the retinal image, with both illumination and image-bearing light traveling along substantially the same optical path. One particularly troublesome problem relates to the need to provide illumination at levels sufficient for imaging and, at the same time, to eliminate stray light caused by unwanted reflection from the cornea that surrounds the pupil. It is difficult to obtain both a wide field of view and sufficient illumination while keeping unwanted reflected light from the optical system.

Figure 1:
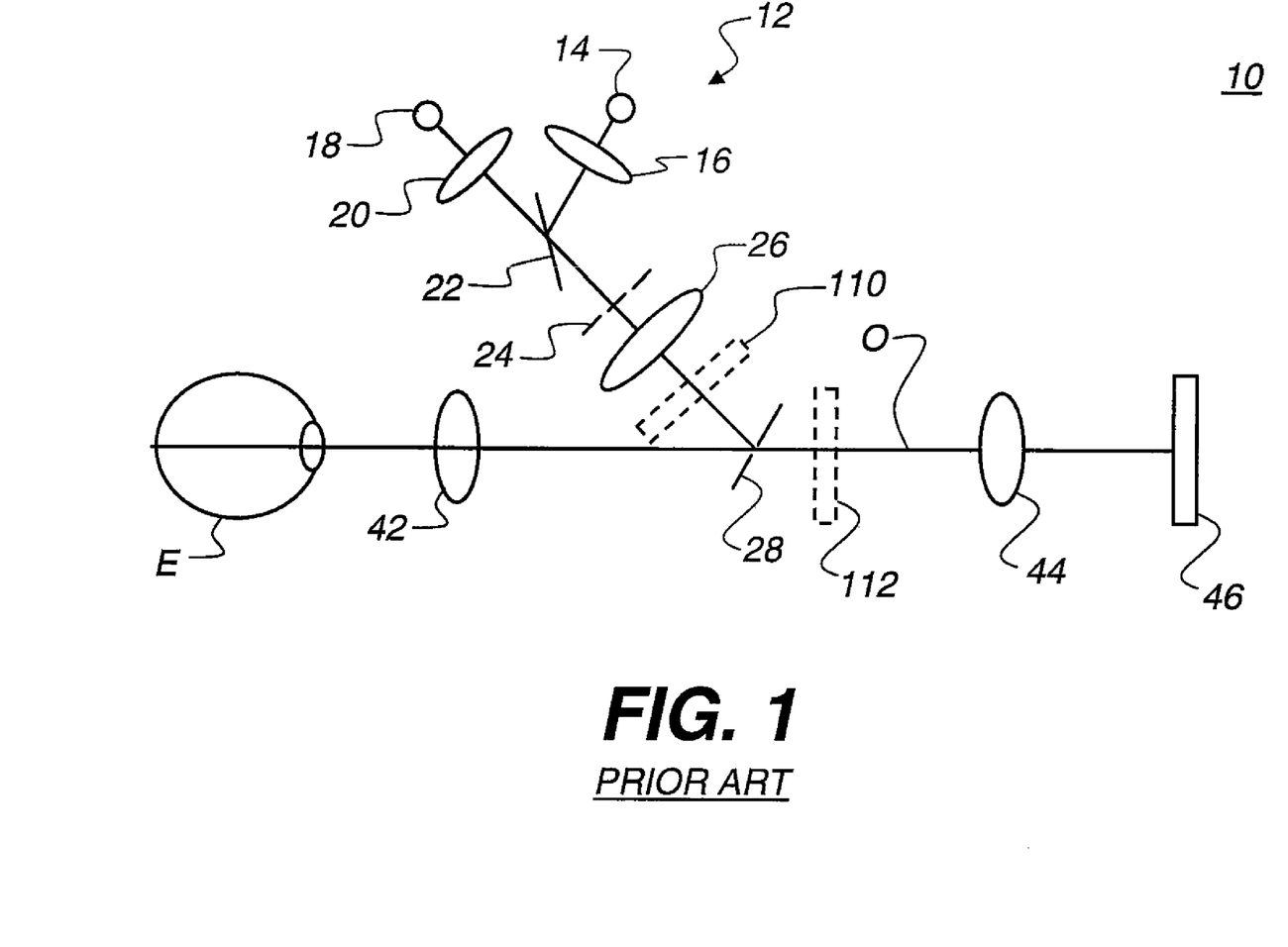
FIG. 1 is a simplified block diagram of a conventional fundus imaging apparatus.

This problem is most readily illustrated by an overview of the operation of the illumination subsystem in a conventional fundus imaging apparatus. Referring to FIG. 1, there is shown a fundus imaging apparatus 10 in which a conventional illumination section 12 is used. The patient's eye E is positioned along an optical axis O using an alignment subsystem (not shown in FIG. 1). Illumination section 12 directs light either from an observation light source 14 and a lens 16 or from an image capture light source 18 and a lens 20 as controlled by control logic circuitry for fundus imaging apparatus 10 (not shown in FIG. 1). A half-mirror 22 directs light from the appropriate source through a ring-slit diaphragm 24 and a lens 26, to an apertured mirror 28. Apertured mirror 28 directs the illumination light along axis O and through an objective lens 42 toward the pupil for illuminating the retina of eye E. Depending on the use of fundus imaging apparatus 10 at any one time, either observation light source 14 or image capture light source 18 are activated. Observation light source 14 is typically infrared (IR) light, to which eye E is insensitive. Image capture light source 18, on the other hand, may be a high-brightness source such as a xenon lamp, for example. Depending on the application, image capture light source 18 may be pulsed or strobed.

Figure 2:
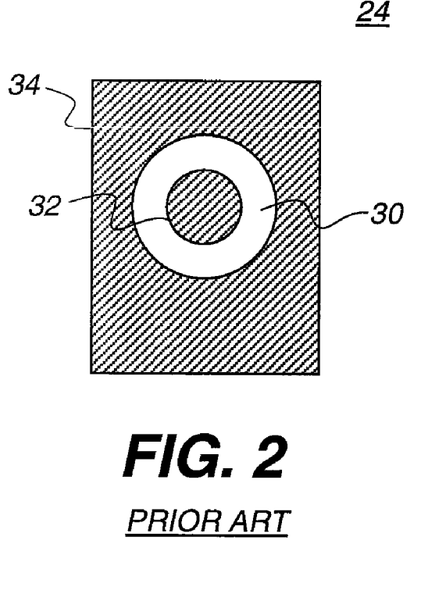
FIG. 2 is a plan view showing a ring-slit diaphragm as used in conventional systems.

Ring-slit diaphragm 24 has the characteristic functional arrangement shown in FIG. 2. Light is transmitted through an inner ring 30 and is blocked at a middle section 32 and at an outer section 34. As is shown in the received illumination ring of FIG. 3, inner ring 30, having an inner radius 41, is directed into a pupil 36 of the patient as a ring 40 of illumination. To obtain the retinal image, apertured mirror 28 (FIG. 1) has an aperture suitably centered about optical axis O to allow light that has been reflected from the retina of eye E and directed through lenses 42 and 44 to reach a sensor 46, such as a charge coupled device (CCD).

The high-level block diagram of FIG. 1 thus gives an overview of illumination section 12 that applies for conventional fundus imaging apparatus. There have been numerous methods disclosed for optimizing the performance of illumination section 12, including components arranged to prevent stray reflected light from the cornea of eye E and from optical surfaces from being directed back toward sensor 46. Referring to the schematic block diagram of FIG. 1, three basic approaches have been followed in order to reduce or eliminate stray light from these sources:

(i) Using a pair of crossed polarizers. Using this approach, a first polarizer 110 is placed in the illumination path, at some position before apertured mirror 28. A second polarizer 112 is then positioned in the image path, at some point between apertured mirror 28 and sensor 46. With reference to FIG. 1, possible locations of first polarizer 110 and second polarizer 112 are shown in phantom. The two polarizers 110 and 112 would be oriented with transmission axes orthogonally disposed with respect to each other.

There are two key problems with this method. The first problem relates to the needed lamp power when using this strategy. Because only that portion of light having the proper polarization is transmitted through polarizer 110, more light is needed from image capture light source 18. The use of second polarizer 112 further reduces the available power. As a result, image capture light source 18 must be about 4 times as bright as would be necessary without polarizers 110 and 112. The second problem relates to the nature of light reflected from the cornea. Since a portion of this light can be depolarized, particularly due to the large incident angle, second polarizer 112 will be less effective in blocking unwanted stray light.

(ii) Blocking light that would otherwise reflect back from the surface of objective lens 42. This solution, however, reduces uniformity of the desired light reflected from the retina, particularly noticeable when attempting to obtain retinal images from near-sighted patients.

(iii) Separating illumination and imaging optical paths. A beamsplitter can be placed in front of objective lens 42 to effect this separation. However, this type of solution requires additional lamp power in order to obtain suitable reflected light from the retina and necessitates a longer working distance for objective lens 42.

Figure 3:
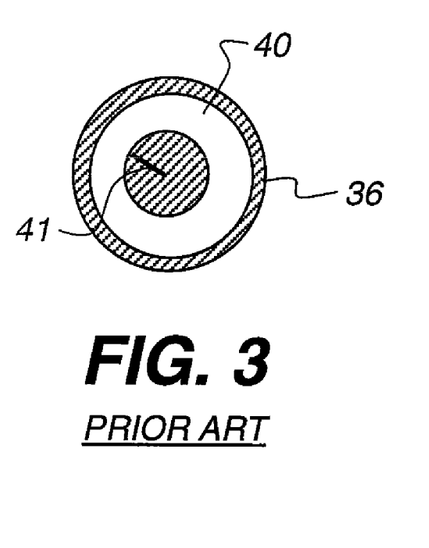
FIG. 3 is a cross section of an illumination ring, taken in a plane normal to the optical axis.

In order to provide uniform illumination without unwanted reflected light from the cornea at the same time, as described with reference to FIGS. 2 and 3, conventional fundus imaging systems require pupil dilation. The disadvantages of pupil dilation include patient inconvenience, lost time, and discomfort. Attempts to design these devices for use with un-dilated pupils have been largely unsuccessful to date, resulting in limited field of view and insufficient illumination for accurate imaging. If the pupil is not dilated, the field of view of the camera can be limited to no more than about 30 degrees, for example, when the pupil diameter is about 3 mm.

As yet another limitation, the size of the illumination ring in conventional fundus imaging systems is either fixed at a single value or is switchable among a small set of discrete values, obtained by inserting different masks or apertures into the optical path. There is no capability for changing the size of the illumination ring in a continuous fashion.

Thus, it can be seen that there is a need for a fundus imaging apparatus having illumination and imaging optics that allow imaging with smaller pupil diameters in order to reduce or eliminate the requirement for pupil dilation. Such a system should provide a suitably wide field of view, adjustability of illumination ring diameter, and good image quality.

SUMMARY OF THE INVENTION

Briefly, according to one aspect of the present invention, a fundus camera for obtaining a retinal image of an eye comprises:
- a light source;
- a ring aperture to form a ring illumination, the ring aperture conjugate to the cornea of said eye;
- a first aperture to control the ring illumination radius, the first aperture conjugate to the iris of said eye;
- an apertured mirror for redirecting the ring illumination from said first aperture toward the eye;
- an objective lens, disposed between the apertured mirror and the eye, with an entrance pupil which lies between the iris of said eye and the cornea of said eye, whereby the objective lens directs the ring illumination into the pupil of the eye and directs a reflected image-bearing light from the retina along an optical axis and through the apertured mirror;
- a second aperture forming an aperture stop for the reflected image-bearing light from the retina, wherein the second aperture is conjugate to a plane lying between the cornea and the iris of said eye;
- a third aperture conjugate to the cornea for blocking light reflected from the cornea; and
- a sensor for providing an image of the retina of said eye from the image-bearing light.

It is an advantage of the present invention that it provides sufficient illumination for retinal imaging without requiring pupil dilation in many cases.

The invention and its objects and advantages will become more apparent in the detailed description of the preferred embodiment presented below.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings, wherein:

DETAILED DESCRIPTION OF THE INVENTION

The following description is directed in particular to elements forming part of, or in cooperation with the apparatus in accordance with the present invention. It is to be understood that elements not specifically shown or described may take various forms well known to those skilled in the art.

Figure 4:
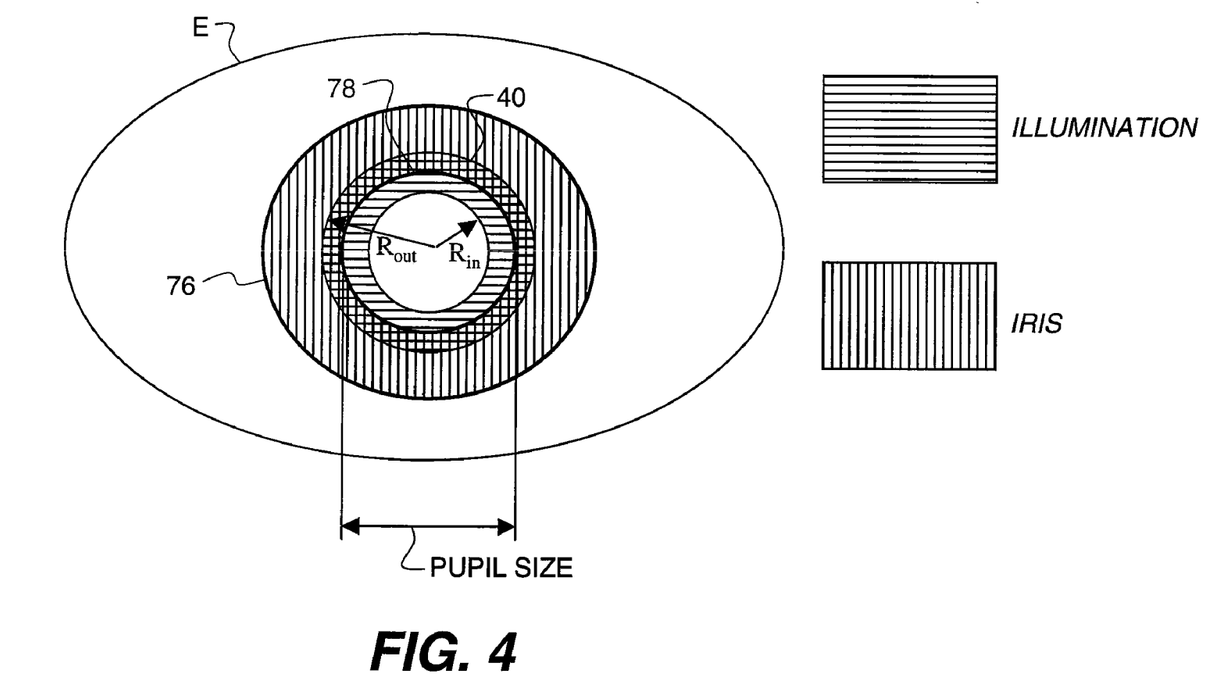
FIG. 4 is a plan view showing areas of the human eye that are of interest for illumination.
Figure 5:
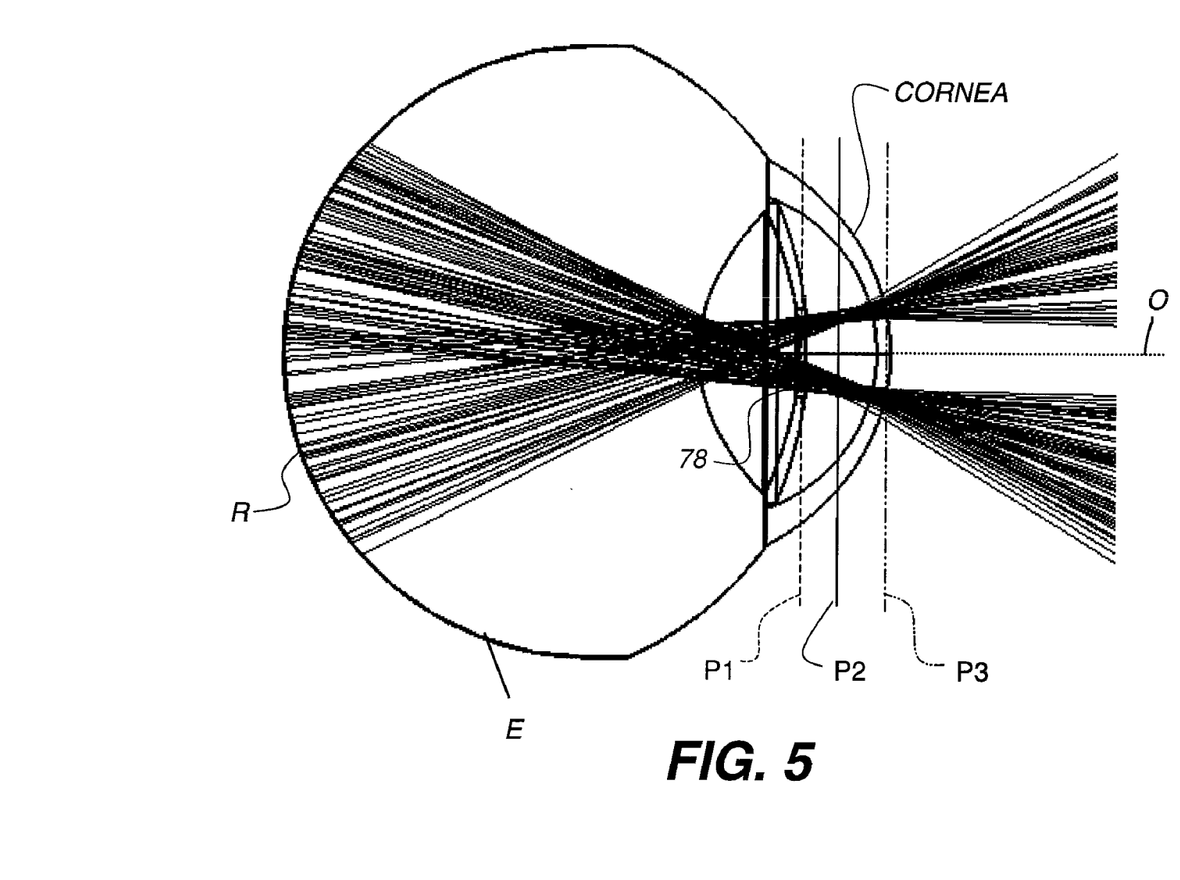
FIG. 5 is a cross-sectional view of the eye showing key reference planes and ray patterns.

In order to better understand novel aspects of the present invention, it is useful to first consider how the eye can be illuminated for retinal imaging. The front and cross-sectional views of FIGS. 4 and 5 show key dimensional, angular, and spatial relationships relevant for this purpose. In FIG. 4, eye E has an iris 76 extending about its pupil 78. For imaging the retina, a ring 40 of illumination is directed toward the eye, centered at the center of pupil 78 and dimensioned so that it provides light around the periphery of pupil 78, without overlap or slight overlap onto iris 76. Radii $R_{in}$ and $R_{out}$ define the width of ring 40 of illumination. Radius $R_{in}$ is controlled by considerations of cornea reflection, illumination uniformity, alignment, power level, and pupil size. Radius $R_{out}$ is determined by factors such as control of iris scattering and pupil size.

The cross-section view of FIG. 5 shows the ray pattern for retinal imaging using a ring of illumination. Three key planes are represented: an iris plane P1, considered to be positioned at the iris; a cornea plane P3, considered to be positioned at the cornea, and a camera entrance pupil plane P2 that lies between planes P1 and P3. Exit pupil plane of the eye is close to the iris plane P1. Plane P2 denotes the position of the entrance pupil of the fundus imaging apparatus in the present invention, as described subsequently.

Figure 6:
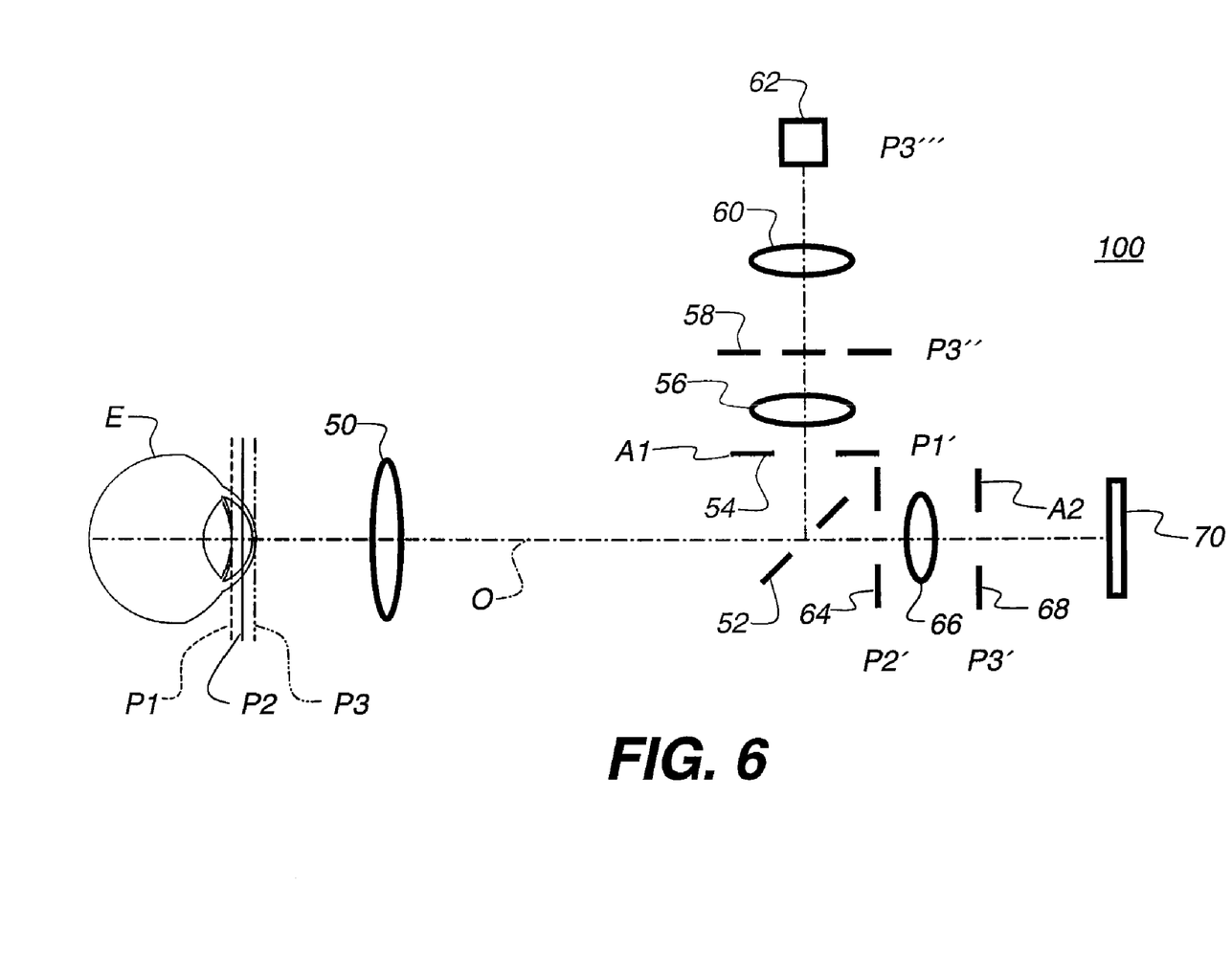
FIG. 6 is a schematic block diagram showing the overall arrangement of an imaging apparatus according to the present invention.

As FIGS. 4 and 5 show, the function of the illumination system is to direct ring 40 of illumination to the retina R, while leaving a central portion along an optical axis O for reflected light from the retina R, bearing the retinal image. A fundus imaging apparatus 100 of the present invention, as shown in the schematic of FIG. 6, utilizes this behavior for retinal imaging in a novel manner, optimizing the delivery of illumination and management of reflected light from the eye. A light source 62 provides the source illumination, optically conditioned by a lens 60, through a ring aperture 58, which forms the ring of illumination. A lens 56 directs this ring of illumination through an aperture 54 at A1 and to an apertured mirror 52. Apertured mirror 52 directs the ring of illumination along optical axis O and through an objective lens 50 to the eye E. Apertured mirror 52 blocks reflected light from the cornea and passes the image-bearing light that travels along axis O. A stop 64 together with another aperture 68 at A2 block leaking light reflected from the cornea. A camera 70 or other sensor obtains the image from the retina.

Conjugate positions in FIG. 6 are indicated using conventional notation. (For example, P3, P3', P3", and P3''' are all optically conjugate through the corresponding lens elements.) For the embodiment of FIG. 6, a number of key functional and spatial relationships apply:

(i) Ring aperture 58 at P3" creates a ring of illumination with a given inner radius on cornea plane P3 and also acts to block unwanted light that, otherwise, will reflect from lens surfaces and reach the sensor. Ring aperture 58 at P3" is conjugate to cornea plane P3 and, through lens 60, to light source 62.

(ii) Aperture 54 at A1 is conjugate to iris plane P1. Aperture 54 at A1 is used to control the pupil size of illumination ring 40. The size of aperture 54 at A1 can be changed in continuous fashion to suit it to the iris size. For example, aperture 54 at A1 can be a liquid crystal spatial light modulator configured to provide an aperture of programmable shape and size.

(iii) Aperture 68 at A2 blocks unwanted light that has been reflected from the cornea. Aperture 68 is conjugate to cornea plane P3 and is needed because the inner radius of ring 40 of illumination may not be large enough.

(iv) Stop 64 is conjugate to camera entrance pupil plane P2, and is thus the effective aperture stop of the optical system. Camera entrance pupil plane P2 itself lies between cornea plane P3 and iris plane P1, as noted earlier.

Figure 7:
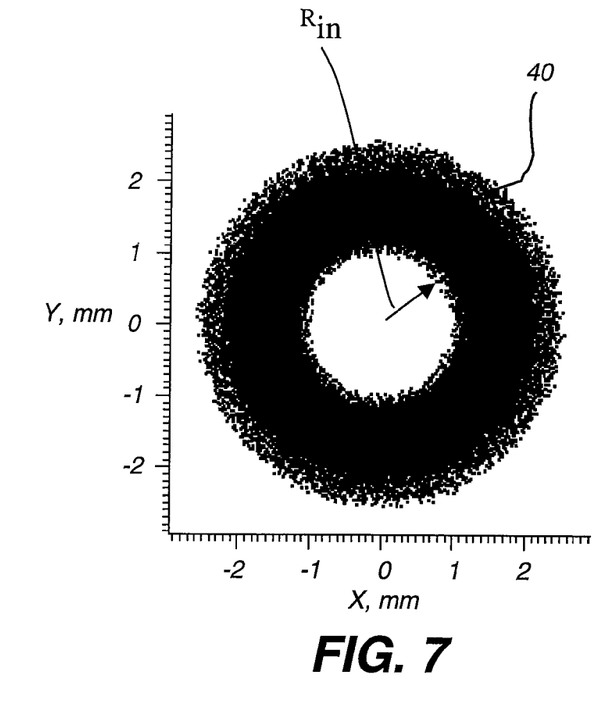
FIG. 7 is a graph showing the arrangement of a ring of illumination provided by the present invention.
Figure 8:
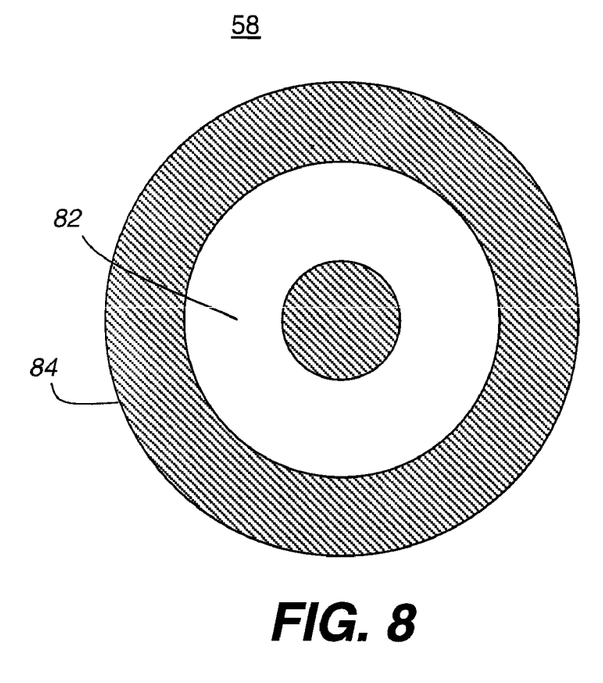
FIGS. 8, 9, and 10 are plan views of aperture masks used in one embodiment.
Figure 9:
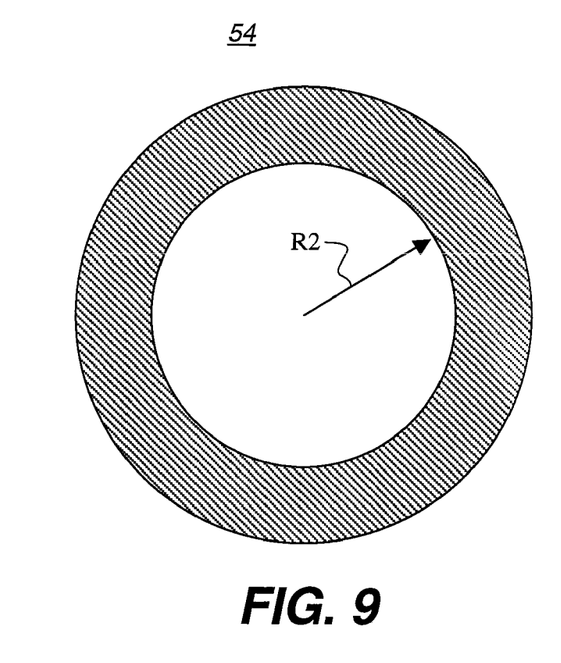

In order to image at a reduced pupil diameter, it is necessary to carefully control ring 40 of illumination. The cooperation of ring aperture 58 (P3") and aperture 54 provide illumination ring 40 to the cornea, as shown in FIG. 7. Ring aperture 58, as shown in FIG. 8, has an opaque section 84 and a circular transparent section 82. Aperture 54, as shown in FIG. 9, controls the size of illumination beam size on the iris.

Figure 10:
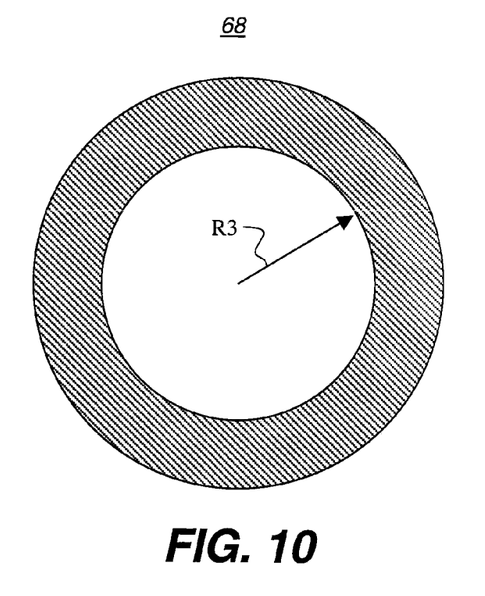

In order to block substantially all of the unwanted reflected light from the cornea, aperture 68 is employed, as shown in FIG. 10. Radius R3 is an inner radius of this mask, determined by the radius $R_{in}$ of illumination ring 40 on the cornea. Aperture 68 may mask a small portion of useful light in some embodiments. The combination of aperture 68 and stop 64 is useful for blocking substantially all of the unwanted reflected light from the cornea.

Using these functional and spatial relationships, fundus imaging apparatus 100 of FIG. 6 is capable of obtaining a retinal image with a large field of view through a small pupil. Earlier designs, utilizing a dilated pupil, located the entrance pupil of the imaging system at the cornea surface. A dilated pupil is generally large enough so that vignetting does not occur with this arrangement. In contrast, fundus imaging apparatus 100 of the present invention locates the entrance pupil of the imaging system near the exit pupil of the eye. This allows imaging when the pupil is of smaller diameter and minimizes or eliminates vignetting, by the iris, of light reflected from the retina. The inner radius R1, shown for ring 40 in FIG. 7 can be small, allowing only enough area for reflected light from the retina to be passed to camera 70.

Figure 11:
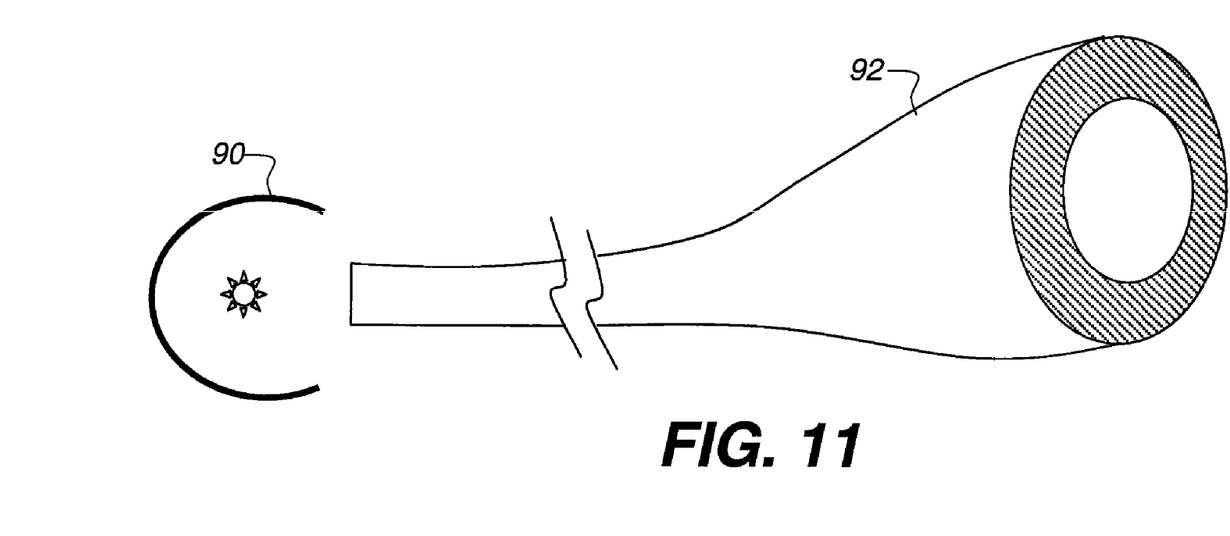
FIG. 11 is a perspective view of an alternate arrangement of illumination components.

FIG. 11 shows one alternative embodiment for ring illumination optics in fundus imaging apparatus 100. In this embodiment, a light source 90 provides light to an optical fiber ring 92. With respect to the block diagram of FIG. 6, the arrangement of FIG. 11 could be substituted for light source 62, lens 60, and aperture 58.

Apertures 54, 58, and 68 may be fixed-size mechanical apertures or may be of adjustable size. One or more of apertures 54, 58, or 68 could be formed using a controllable light gating device such as a transmissive liquid crystal (LC) spatial light modulator, for example. Masked regions of these apertures could be variably sized using an LC spatial light modulator, or adjustable shutter, allowing adjustment for the patient's pupil size or dimensions, for example.

Rotating Mask Embodiment

Figure 12:
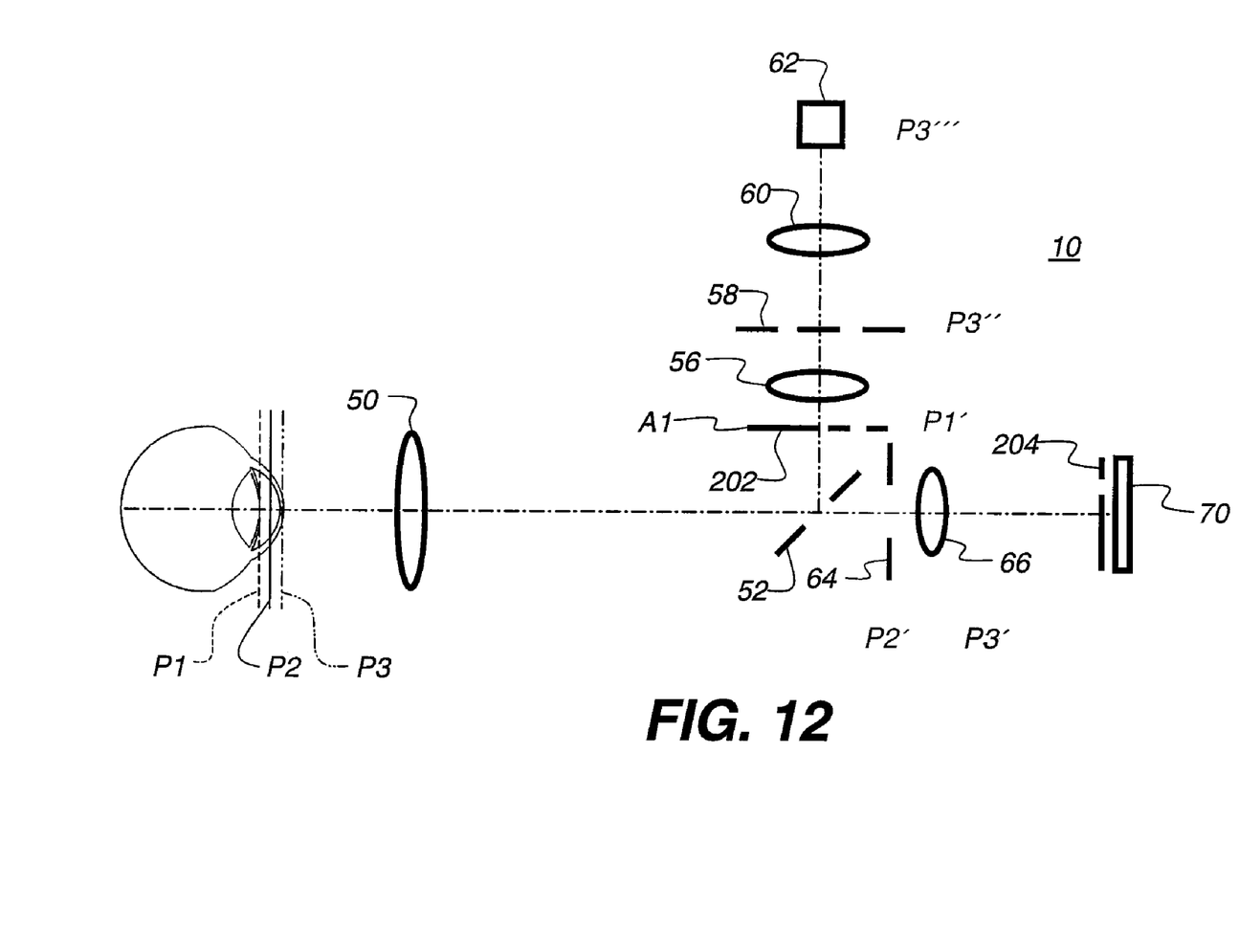
FIG. 12 is a schematic block diagram showing the overall arrangement of an imaging apparatus according another embodiment of the present invention.
Figure 13:
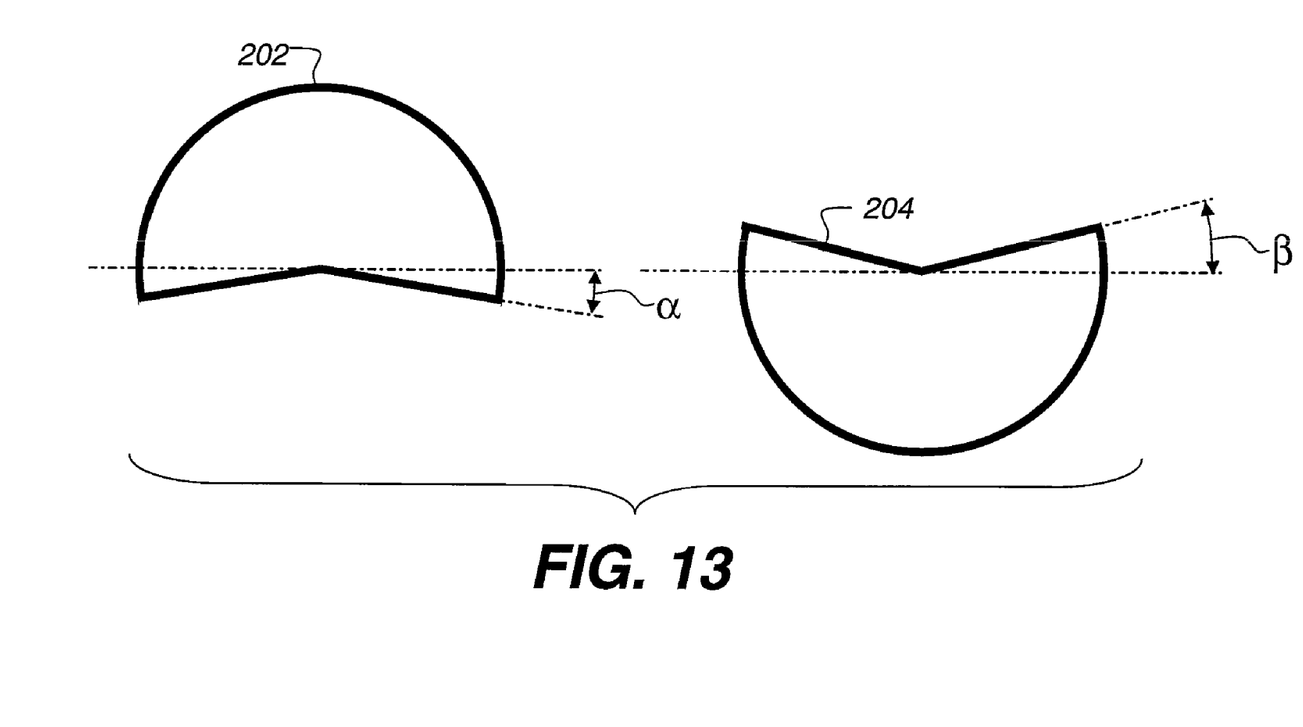
FIG. 13 is a plan view of rotating masks in an alternate embodiment.
Figure 14:
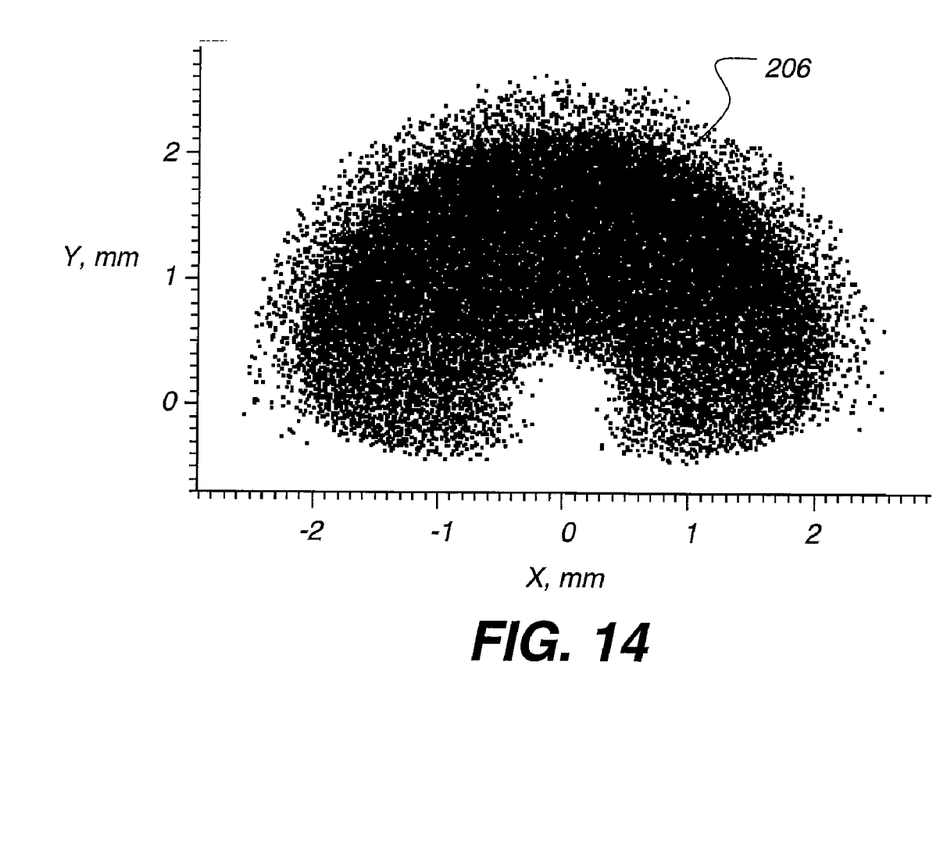
FIG. 14 is a graph showing the arrangement of a rotated ring of illumination according to an alternate embodiment of the present invention.

Referring to FIG. 12, there is shown an alternate embodiment using rotating masks 202 and 204. FIG. 13 shows rotating masks 202 and 204 in plan view. Mask 202 is placed at position A1, conjugate to iris plane P1. Rotating mask 204 is disposed near sensor 70. In effect, rotating mask 202 splits the pupil; rotating mask 204 splits the field. With rotating mask 202 at iris plane P1', the cornea and pupil of the eye are partially illuminated, with the pattern of illumination shown in FIG. 14 as a partial ring 206. A full rotation of rotating mask 202 is needed in order to illuminate the whole pupil. With rotating mask 204, only a portion of the retina is imaged to sensor 70 at one time, so that a full rotation of both rotating masks 202 and 204 is necessary in order to obtain the full retinal image. Mask 204 effectively blocks light reflected from the cornea, allowing only image light to reach sensor 70. Careful alignment and angular orientation of rotating masks 202 and 204 with respect to each other is required in order to obtain the retina image without unwanted reflected light.

Opening angles α and β for masks 202 and 204 are arranged so that α is less than β. This allows mask 204 to block light reflected from the cornea even where there is slight aberration.

Figure 15:
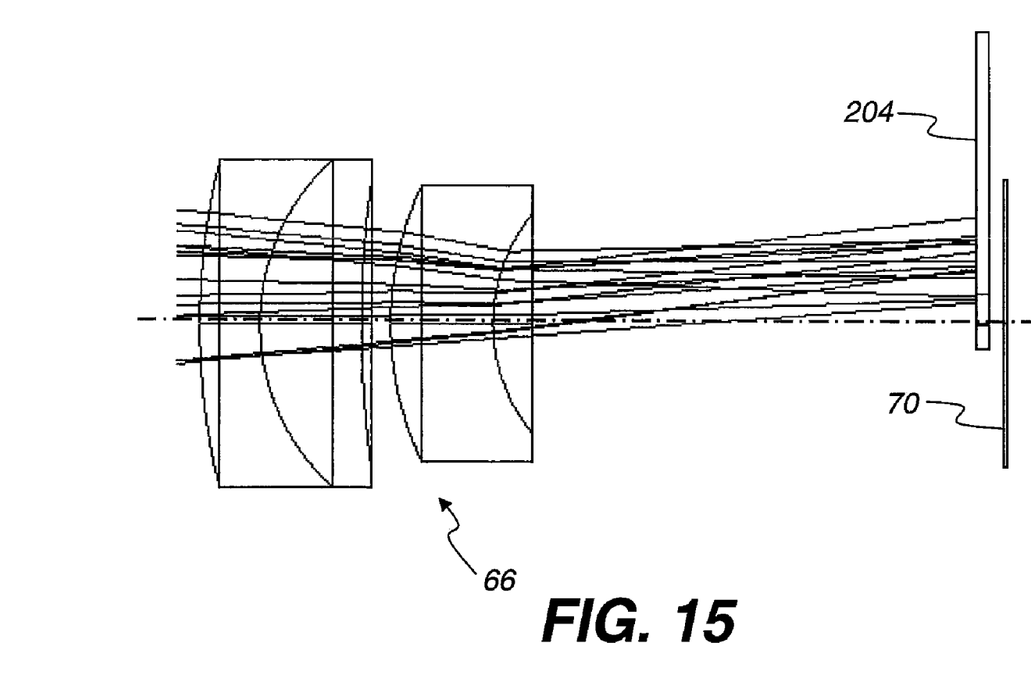
FIG. 15 is a side view showing components used when employing a rotatable mask.

FIG. 15 shows a side view of components in a portion of the imaging path when using rotating masks 202 and 204. Here, rays traced indicate reflected light from the cornea for given positions of rotating masks 202 and 204. At each rotational position, rotating mask 204 effectively blocks this reflected light from reaching sensor 70. In this way, this method may provide advantageous over providing the complete illumination ring 40 at one time by reducing the amount of stray light reflected from lenses 66 and other optical components, for example.

The invention has been described in detail with particular reference to certain preferred embodiments thereof, but it will be understood that variations and modifications can be effected within the scope of the invention. Thus, what is provided is a fundus camera with a wide field of view for small pupil sizes.

PARTS LIST

| | |
|---|---|
| 10 | fundus imaging apparatus |
| 12 | illumination section |
| 14 | observation light source |
| 16 | lens |
| 18 | image capture light source |
| 20 | lens |
| 22 | half-mirror |
| 24 | ring-slit diaphragm |
| 26 | lens |
| 28 | apertured mirror |
| 30 | inner ring |
| 32 | middle section |
| 34 | outer section |
| 36 | pupil |

-continued

| 40 | ring |
| 41 | inner radius |
| 42 | lens |
| 44 | lens |
| 46 | sensor |
| 50 | objective lens |
| 52 | apertured mirror |
| 54 | aperture |
| 56 | lens |
| 58 | ring aperture |
| 60 | lens |
| 62 | light source |
| 64 | stop |
| 66 | lens |
| 68 | aperture |
| 70 | camera |
| 76 | iris |
| 78 | pupil |
| 82 | transparent section |
| 84 | opaque section |
| 90 | light source |
| 92 | optical fiber ring |
| 100 | fundus imaging apparatus |
| 110 | polarizer |
| 112 | polarizer |
| 202 | rotating mask |
| 204 | rotating mask |
| 206 | partial ring |

The invention claimed is:

1. A fundus camera for obtaining a retinal image of an eye comprising:
   a light source;
   a ring aperture to form a ring illumination, the ring aperture conjugate to a cornea of the eye;
   a first rotating mask providing a moving aperture to provide a portion of the ring illumination at a time, the first rotating mask conjugate to the iris of the eye;
   an aperture mirror for redirecting the ring illumination from the first rotating mask toward the eye;
   an objective lens, disposed between the aperture mirror and the eye, with an entrance pupil which lies between the iris of the eye and the cornea of the eye, whereby the objective lens directs the ring illumination into the pupil of the eye and directs a reflected image-bearing light from a retina along an optical axis and through the apertured mirror;
   an aperture stop for the reflected image-bearing light from the retina, wherein the aperture stop is conjugate to a plane lying between the cornea and the iris of the eye; and
   a second rotating mask in the path of image-bearing light from the retina to provide a portion of the image bearing light to a sensor.

2. A fundus camera according to claim 1 wherein the ring aperture comprises a spatial light modulator.

3. The fundus camera according to claim 1, wherein the light source comprises a plurality of optical fibers.

4. A method for obtaining a retinal image of an eye comprising:
   providing a light source;
   forming a ring aperture to provide a ring illumination, the ring aperture conjugate to a cornea of the eye;
   providing a first rotating mask to transmit a portion of the ring illumination at a time, the first rotating mask conjugate to an iris of the eye;
   directing the portion of the ring illumination from the ring aperture toward the eye through an apertured mirror;
   disposing an objective lens between the aperture mirror and the eye, with an entrance pupil which lies between the iris of the eye and a cornea of the eye, whereby the objective lens directs the portion of ring illumination into the pupil of the eye and directs a reflected image-bearing light from a retina along an optical axis and through the apertured mirror;
   disposing an aperture stop conjugate to a plane lying between the cornea and the iris of the eye for the reflected image-bearing light from the retina;
   disposing a second rotating mask conjugate to the cornea for blocking light reflected from the cornea; and
   obtaining a partial image of the retina of the eye from the image-bearing light at a sensor.

5. The method of claim 4, wherein the light source comprises a plurality of optical fibers.

* * * * *